US009745538B2

(12) United States Patent
Dennis et al.

(10) Patent No.: US 9,745,538 B2
(45) Date of Patent: *Aug. 29, 2017

(54) METHODS OF RECOVERING OIL FROM MICROORGANISMS

(71) Applicant: MARA Renewables Corporation, Dartmouth (CA)

(72) Inventors: Dorothy A. Dennis, Halifax (CA); Roberto E. Armenta, Dartmouth (CA)

(73) Assignee: MARA RENEWABLES CORPORATION, Nova Scotia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,471

(22) Filed: Dec. 19, 2014

(65) Prior Publication Data

US 2015/0176042 A1    Jun. 25, 2015

Related U.S. Application Data

(60) Provisional application No. 61/918,886, filed on Dec. 20, 2013.

(51) Int. Cl.
*C12P 7/64* (2006.01)
*C11B 1/10* (2006.01)

(52) U.S. Cl.
CPC .............. *C11B 1/10* (2013.01); *C12P 7/6427* (2013.01); *C12P 7/6463* (2013.01); *C12P 7/6472* (2013.01)

(58) Field of Classification Search
CPC ..................................... C12P 7/64; C11B 1/10
See application file for complete search history.

(56) References Cited

U.S. PATENT DOCUMENTS

| | | | |
|---|---|---|---|
| 2,753,362 | A | 7/1956 | Owades et al. |
| 3,089,821 | A | 5/1963 | Folkers |
| 4,504,473 | A | 3/1985 | Cantrell |
| 4,720,456 | A | 1/1988 | Wagner et al. |
| 4,792,418 | A | 12/1988 | Rubin et al. |
| 4,906,746 | A | 3/1990 | Barnier et al. |
| 5,130,242 | A | 7/1992 | Barclay |
| 5,173,409 | A | 12/1992 | English |
| 5,179,012 | A | 1/1993 | Gudin et al. |
| 5,338,673 | A | 8/1994 | Thepenier et al. |
| 5,340,594 | A | 8/1994 | Barclay |
| 5,340,742 | A | 8/1994 | Barclay |
| 5,397,591 | A | 3/1995 | Kyle et al. |
| 5,492,938 | A | 2/1996 | Kyle |
| 5,539,133 | A | 7/1996 | Kohn et al. |
| 5,897,994 | A | 4/1999 | Sandoz et al. |
| 5,928,696 | A | 7/1999 | Best et al. |
| 6,166,231 | A | 12/2000 | Hoeksema |
| 6,180,376 | B1 | 1/2001 | Liddell |
| 6,255,505 | B1 | 7/2001 | Bijl et al. |
| 6,344,349 | B1 | 2/2002 | Moldavsky et al. |
| 6,451,567 | B1 | 9/2002 | Barclay |
| 6,509,178 | B1 | 1/2003 | Tanaka et al. |
| 6,582,941 | B1 | 6/2003 | Yokochi et al. |
| 6,607,900 | B2 | 8/2003 | Bailey et al. |
| 6,750,048 | B2 | 6/2004 | Ruecker et al. |
| 6,812,001 | B2 | 11/2004 | Sibeijn et al. |
| 7,351,558 | B2 | 4/2008 | Ruecker et al. |
| 7,431,952 | B2 | 10/2008 | Bijl et al. |
| 7,662,598 | B2 | 2/2010 | Ruecker et al. |
| 7,781,193 | B2 | 8/2010 | Ruecker et al. |
| 2005/0170479 | A1* | 8/2005 | Weaver .................... A23D 9/00 435/134 |
| 2008/0038800 | A1 | 2/2008 | Ruecker et al. |
| 2008/0044876 | A1 | 2/2008 | Ruecker et al. |
| 2009/0117194 | A1 | 5/2009 | Burja et al. |
| 2012/0244584 | A1 | 9/2012 | Zhang et al. |
| 2014/0212936 | A1 | 7/2014 | Ruecker et al. |

FOREIGN PATENT DOCUMENTS

| | | |
|---|---|---|
| CA | 2076018 | 5/2000 |
| CA | 2397655 | 7/2001 |
| CA | 2611324 | 6/2007 |
| CA | 2146235 | 12/2011 |
| CA | 2801011 | 12/2011 |
| DE | 2056896 A1 | 8/1971 |
| DE | 2056896 B2 | 12/1979 |
| EP | 0969086 A1 | 1/2000 |
| EP | 1178118 | 2/2002 |
| EP | 1305440 B1 | 6/2010 |

(Continued)

OTHER PUBLICATIONS

Atkinson et al., Biochemical engineering and biotechnology handbook, Edition 2, 1991, Macmillan Publishers Ltd , 918-923.

Bennemann et al., Systems and economic analysis of microalgae ponds for conversion of $CO_2$ to biomass, Final Report to the Department of Energy Technology Center, Mar. 21, 1996, 14-27, 124-144.

Cartens et al., Eicosapentaenoic Acid (20:5n-3) from the marine microalga *Phaeodactylum tricornutum*, J. Am. Oil. Chem. Soc., 1996, 73:8, 1025-1031.

Chisti et al., Disruption of microbial cells for intracellular products, Enzyme Microb. Technol., vol. 8, Apr. 1986, 194-204.

Ensanni E., Fundamental parameters in extraction of lipids from wasterwater-grown microalgal biomass, Dissertation Thesis, Department of Civil Engineering, University of California, Berkeley, 1987, 1-71, 170-174.

Hampson et al., Extraction of Lipid-Grown Bacterial Cells by Supercritical Fluid and Organic Solvent to Obtain Pure Medium Chain-Length Polyhydroxyalkanoates, J. Am. Oil. Chem. Soc., vol. 76, No. 1, 1999, 1371-1374.

(Continued)

*Primary Examiner* — Taeyoon Kim
*Assistant Examiner* — Tiffany Gough
(74) *Attorney, Agent, or Firm* — Kilpatrick Townsend & Stockton, LLP

(57) ABSTRACT

Provided herein are methods of recovering oil from microorganisms. The methods are useful, for example, in obtaining nutritional oils and/or lipid biofuels. The methods of recovering oil described herein include contacting a population of microorganisms with one or more enzymes under conditions that cause disruption of the microorganisms, concentrating the disrupted microorganisms, and extracting lipids from the disrupted microorganisms at high temperature in the presence of a salt and in the absence of solvent.

25 Claims, 5 Drawing Sheets

(56) References Cited

FOREIGN PATENT DOCUMENTS

| | | |
|---|---|---|
| EP | 1252324 B1 | 10/2010 |
| GB | 808128 A | 1/1959 |
| JP | 04211366 A2 | 8/1992 |
| JP | H08509355 A | 10/1996 |
| JP | H1072590 A | 3/1998 |
| JP | H11116983 A2 | 4/1999 |
| JP | H11285376 A2 | 10/1999 |
| WO | 8808025 A1 | 10/1988 |
| WO | 9107498 A1 | 5/1991 |
| WO | 9408467 A1 | 4/1994 |
| WO | 9605278 A1 | 2/1996 |
| WO | 9621037 A1 | 7/1996 |
| WO | 9704121 | 2/1997 |
| WO | 9704121 A1 | 2/1997 |
| WO | 9736996 A2 | 10/1997 |
| WO | 9737032 | 10/1997 |
| WO | 9737032 A2 | 10/1997 |
| WO | 9803671 A2 | 1/1998 |
| WO | 9850574 A2 | 11/1998 |
| WO | 9932604 A2 | 7/1999 |
| WO | 0153512 | 7/2001 |
| WO | 0153512 A1 | 7/2001 |
| WO | 0210423 | 2/2002 |
| WO | 0210423 A2 | 2/2002 |
| WO | 03092628 A2 | 11/2003 |
| WO | WO2011153246 A3 * 12/2011 ................ C12P 7/64 |  |

OTHER PUBLICATIONS

Hruschka et al., Dans Oléagineux Corps, A new oil extraction process: FRIOLEX, Lipides, vol. 5(5), 1998, 356-360.

Medina et al., Downstream processing of algal polyunsaturated fatty acids, Biotechnology Advances, vol. 16, 1998, 517-580.

Middelberg, A., Process Scale Disruption of Microroganisms, Biotechnology Advances, vol. 13, No. 3, 1995, 491-551.

Oils & Fats International, "Alternative Methods of Extractions", 6:29-32, 1992.

Pinkart et al., Rapid separation of microbial lipids using solid phase extraction columns, Journal of microbiological methods, Sep. 1998, vol. 34, No. 1, 9-15, Abstract only.

Pythium, from Wikipedia, the free encyclopedia, http://en.wikipedia.org/wiki/Pythium, printed Feb. 16, 2008, 2 pages.

Ratledge et al., Down-stream processing, extraction, and purification of single cell oils, Single Cell Oils, Chapter 13, Apr. 2005, 202-219.

Robles et al., Lipase-catalyzed esterification of glycero and polyunsaturated fatty acids from fish and microalgae oils, Journal of Biotechnology, vol. 70, Apr. 30, 1999, No. 1-3, 379-391, Abstract only.

Sawayama et al., Possibility of renewable energy production and $CO_2$ mitigation by thermochemical liquefaction of microalgae, Biomass and Bioenergy, 1999, vol. 17, 33-39.

Shimizu et al., Production of a novel omega-1 eicosapentaenoic acid by mortierella-alpina 1s-4 grown on 1 hexadecene, Archives of Microbiology, 1991, vol. 156, No. 3, 163-166, Abstract only.

Spellman et al., Proteinase and exopeptidase hydrolysis of whey protein: Comparison of the TNBS, OPA and pH stat methods for quantification of degree of hydrolysis, International Dairy Journal, 2003, 13: 447-453.

Totani et al., Industrial Production of Arachidonic Acid by Mortierella, Industrial Application of Single Cell Oils, 1992, Chapter 4.

Wynn et al., The role of malic enzyme in the regulation of lipid accumulation in filamentous fungi, Microbiology, vol. 145, 1999, 1911-1917.

International PCT application No. PCT/IB2014/003136, International Search Report and Written Opinion, mailed May 12, 2015, 11 pages.

International PCT application No. PCT/IB2014/003113, International Search Report and Written Opinion, mailed May 6, 2015, 14 pages.

Chen et al., "Subcritical co-solvents extraction of lipid from wet microalgae pastes of *Nannochloropsis* sp.", European Journal of Lipid Science and Technology, 114(2): 205-212 (2011).

Liang et al., "Enzyme-assisted aqueous extraction of lipid from microalgae", Journal of Agricultural and Food Chemistry, 60(47): 11771-11776 (2012).

U.S. Appl. No. 14/862,862, Office Action mailed Nov. 6, 2015, 15 pages.

Extended search report in related EP Application No. 14871148 mailed Oct. 28, 2016.

Lowrey, et al., "Nutrient recycling of lipid-extracted waste in the production of an oleaginous thraustochytrid," Applied Microbiology and Biotechnology, vol. 100, No. 10, Mar. 22, 2016, pp. 4711-4721.

Lowrey, et al., "Sequential recycling of enzymatic lipid-extracted hydrolysate in fermentations with a thraustochytrid," Bioresource Technology, vol. 209, Jun. 2016, pp. 333-342.

* cited by examiner

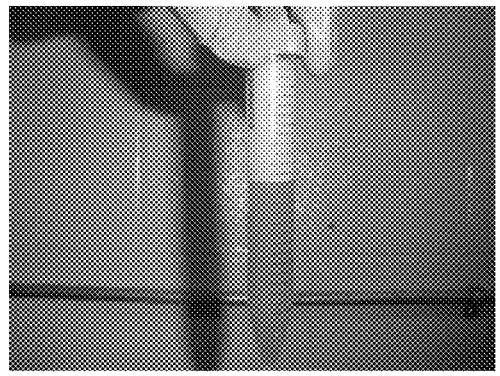 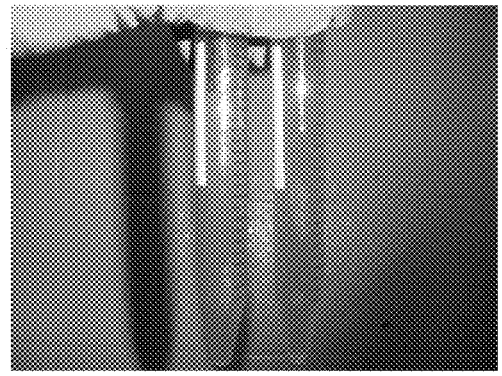
Figure 7A             Figure 7B
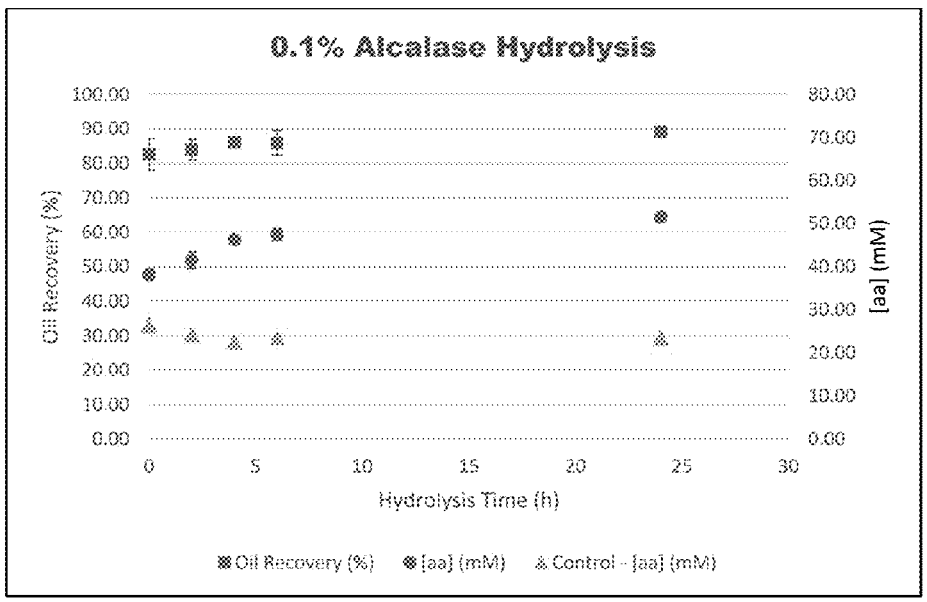
Figure 8

METHODS OF RECOVERING OIL FROM MICROORGANISMS

CROSS-REFERENCE TO RELATED APPLICATIONS

This application claims the benefit of U.S. provisional application No. 61/918,886, filed Dec. 20, 2013, which is incorporated herein by reference in its entirety.

BACKGROUND

Oil can be recovered from microorganisms, such as microalgae, using wet extraction methods or dry extraction methods. In dry extraction methods, microorganisms are typically harvested and dried before oil extraction. However, drying is an expensive and energy-intensive process. Also, if the oil is rich in polyunsaturated fatty acids (PUFA) (e.g., for food and nutritional supplement applications), the process can cause significant oxidations of the PUFA due to high temperatures involved in drying.

Furthermore, dry extraction methods of recovering oil from microorganisms typically are conducted with organic solvents, such as hexanes, and require coupling with mechanical cell disruption methods for suitable oil yields. However, mechanical disruption methods are expensive and energy intensive, while organic solvents are flammable, toxic, and must be removed from the end oil product.

SUMMARY

Provided herein are wet, solventless methods of recovering oil (i.e., lipids) from microorganisms. The methods are useful, for example, in obtaining nutritional oils and/or lipid biofuels. The methods of recovering oil described herein optionally can be performed as an integrated bioprocess, i.e., as a "one-pot" method.

The methods of recovering lipids from a population of microorganisms described herein comprise contacting the population of microorganisms with one or more enzymes under conditions that cause disruption of the microorganisms, concentrating the disrupted microorganisms, and extracting lipids from the disrupted microorganisms at a high temperature in the presence of a salt and in the absence of organic solvents. Optionally, the contacting step occurs in fermentation medium. Optionally, the contacting step can be performed at a pH between and including 5 to 8.5 (e.g., about 8). The contacting step optionally is performed at a temperature between and including about 50° C. to about 70° C. The contacting step can be performed for one to twenty hours, inclusively (e.g., for one to eight hours, or for four hours).

Optionally, the enzyme used in the contacting step is a protease. The enzyme is optionally Alcalase 2.4 L. Optionally, the enzyme is at a concentration of about 0.001% to about 0.4% volume/volume (inclusively) (e.g., between 0.05 and 0.2, or at about 0.05, 0.1, or 0.2%). The contacting step optionally can be performed in the presence of between 0.05 and 0.2% (inclusively) enzyme for and including one to eight hours at 55° C. For example, the contacting step can be performed in the presence of 0.1% enzyme for four hours at 55° C. Optionally, the contacting step is performed in the presence of 0.05% enzyme for six hours at 55° C. The pH can be titrated to a pH of about 8.0 during the contacting step.

Optionally, the contacting step can include mixing that occurs by aeration or by recirculation. Optionally, the mixing does not occur by agitation.

The contacting step can be performed in the absence of surfactants. Optionally, the population of microorganisms is not concentrated prior to the contacting step. The method can further comprise a pre-treatment step, wherein the pre-treatment step includes disrupting the cells prior to the contacting step. The pre-treatment step can be performed using a chemical, mechanical, or enzymatic cell disruption method.

The concentrating step optionally comprises centrifugation. Optionally, the concentrating step comprises 25% to 95% aqueous removal, inclusively, (e.g., 50% to 95% or 85% aqueous removal).

The high temperature during the extraction step can be from 55° C. to 95° C. (e.g., 75 to 95, or 85° C. or 90° C.). Optionally, the concentration of salt added during the extraction step is from and including 1% to 5% or from 3% to 5% (e.g., 3% or 5%). The salt in the extraction step can be sodium sulfate. At least 80% of lipids can be extracted from the disrupted microorganisms. The extracting step can be performed in the presence of oil (e.g., coconut oil) or biofuel or can be performed in the absence of oil or biofuel.

Optionally, the methods of extracting lipids from a population of microorganisms described herein lack a pasteurization step. Optionally, the methods of extracting lipids from a population of microorganisms described herein lack a drying step.

The population of microorganisms can be selected from the group consisting of algae, fungi, bacteria, and protists. Optionally, the population of microorganisms is selected from the genus *Thraustochytrium, Schizochytrium*, or mixtures thereof. Optionally, the population of microorganisms is a *Thraustochytrium* sp., for example, as deposited as ATCC Accession No. PTA-6245.

The details of one or more embodiments are set forth in the drawings and the description below. Other features, objects, and advantages will be apparent from the description and drawings, and from the claims.

DESCRIPTION OF DRAWINGS

FIG. 7A is a depiction of concentrated hydrolyzed biomass feed treated with Na2SO4 and 90 C heat.

FIG. 7B is a photograph showing (left) spent biomass after centrifugation at 90 C and (right) oil recovered after centrifugation at 90 C.

FIG. 8 is a graph showing the percentage of oil recovered from cells and the amino acid concentration in the media after enzymatic hydrolysis with 0.1% (v/v) Alcalase at 55° C. and pH 8.0 as a function of hydrolysis time.

DETAILED DESCRIPTION

Figure 1:
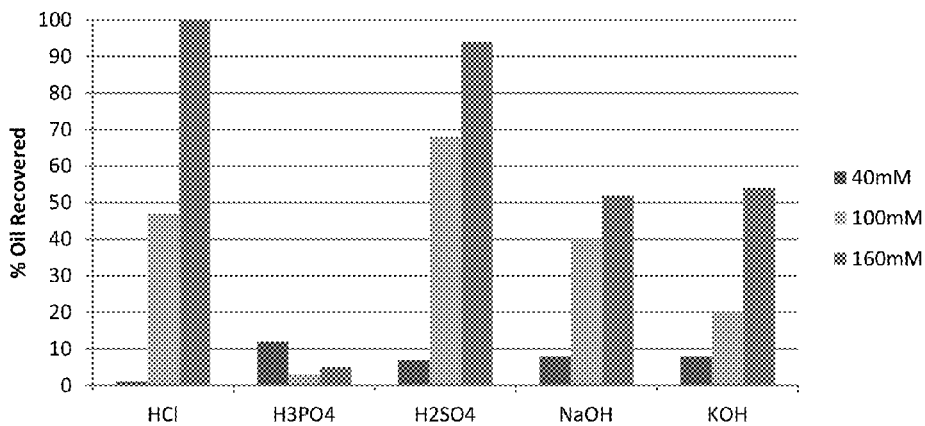
FIG. 1 is a graph showing the percentage of oil recovered from cells hydrolyzed with 40 mM (left bar), 100 mM (middle bar), and 160 mM (right bar) of hydrochloric acid, phosphoric acid, sulfuric acid, sodium hydroxide, and potassium hydroxide.

Described herein are wet, solventless methods of recovering lipids from a population of microorganisms. The methods of recovering lipids include contacting the population of microorganisms with one or more enzymes under conditions that cause disruption of the microorganisms, concentrating the disrupted microorganisms, and extracting lipids from the disrupted microorganisms. The cell disruption is wet. The extraction is performed at a high temperature, in the presence of a salt, and in the absence of solvents. The methods described herein can be referred to as a "one-pot" or "integrated" processes because the microbial oil production and cell disruption to release the oil optionally can be performed within the same vessel. Therefore, the downstream processing steps (e.g., oil extraction and recovery) can be integrated at the end of the upstream processing steps (e.g., fermentation).

I. Microorganisms

The methods described herein include recovering lipids from a population of microorganisms. The population of microorganisms described herein can be algae (e.g., microalgae), fungi (including yeast), bacteria, or protists. Optionally, the microorganism includes Thraustochytrids of the order Thraustochytriales, more specifically Thraustochytriales of the genus *Thraustochytrium* and *Schizochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18).

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyll (e.g., oxycarotenoids), hydrocarbons, and other lipids known to one of ordinary skill in the art.

Optionally, the lipid compounds include saturated, monounsaturated, and/or polyunsaturated fatty acids.

Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, and polyunsaturated compounds.

II. Process
Fermentation

The microorganisms described herein can be cultured according to methods known in the art. For example, a Thraustochytrid, e.g., a *Thraustochytrium* sp., can be cultivated according to methods described in U.S. Patent Publication US 2009/0117194 or US 2012/0244584, which are herein incorporated by reference in their entireties. Microorganisms are grown in a growth medium (also known as "culture medium"). Any of a variety of media can be suitable for use in culturing the microorganisms described herein. Optionally, the medium supplies various nutritional components, including a carbon source and a nitrogen source, for the microorganism.

Optionally, the microorganisms provided herein are cultivated under conditions that increase biomass and/or production of a compound of interest (e.g., oil or total fatty acid (TFA) content). Thraustochytrids, for example, are typically cultured in saline media. Optionally, Thraustochytrids can be cultured in medium having a salt concentration from about 2.0 g/L to about 50.0 g/L. Optionally, Thraustochytrids are cultured in media having a salt concentration from about 2 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 5 g/L to about 20 g/L (e.g., from about 5 g/L to about 15 g/L). The culture media optionally include NaCl. Optionally, the media include natural or artificial sea salt and/or artificial seawater.

The chloride concentration in culture media can be reduced (i.e., lower in amount) as compared to traditional methods. The culture media can include non-chloride-containing sodium salts (e.g., sodium sulfate) as a source of sodium. For example, a significant portion of the total sodium can be supplied by non-chloride salts such that less than about 100%, 75%, 50%, or 25% of the total sodium in culture media is supplied by sodium chloride.

Optionally, the culture media have chloride concentrations of less than about 3 g/L, 500 mg/L, 250 mg/L, or 120 mg/L. For example, culture media have chloride concentrations of between and including about 60 mg/L and 120 mg/L. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein.

Media for Thraustochytrid culture can include any of a variety of carbon sources. Examples of carbon sources include fatty acids; lipids; glycerols; triglycerols; carbohydrates such as glucose, starch, celluloses, hemicelluloses, fructose, dextrose, xylose, lactulose, galactose, maltotriose, maltose, lactose, glycogen, gelatin, starch (corn or wheat), acetate, m-inositol (derived from corn steep liquor), galacturonic acid (derived from pectin), L-fucose (derived from galactose), gentiobiose, glucosamine, alpha-D-glucose-1-phosphate (derived from glucose), cellobiose, dextrin, and alpha-cyclodextrin (derived from starch); sucrose (from molasses); polyols such as maltitol, erythritol, adonitol and oleic acids such as glycerol and tween 80; amino sugars such as N-acetyl-D-galactosamine, N-acetyl-D-glucosamine and N-acetyl-beta-D-mannosamine; and any kind of biomass or waste stream.

Optionally, media include carbon sources at a concentration of about 5 g/L to about 200 g/L. Media can have a C:N (carbon to nitrogen) ratio between about 1:1 and about 40:1.

When two-phase cultures are used, media can have a C:N ratio of between and including about 1:1 to about 5:1 for the first phase, then about 1:1 to about 1:~0 (i.e., no or minimal nitrogen) in the second phase. As used herein, the term minimal refers to less than about 10% (e.g., less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1%). For example, minimal nitrogen in media can refer to less than about 10% (e.g., less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1%) of nitrogen in the media.

Media for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable media typically range between and including about 1 g/L and about 25 g/L.

The media optionally include a phosphate, such as potassium phosphate or sodium-phosphate. Inorganic salts and trace nutrients in media can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium is adjusted to a pH from 4.0 to 6.5, inclusively. The medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Cells can be cultivated for anywhere from 1 day to 60 days. Optionally, cultivation is carried out for 14 days or less, 13 days or less, 12 days or less, 11 days or less, 10 days or less, 9 days or less, 8 days or less, 7 days or less, 6 days or less, 5 days or less, 4 days or less, 3 days or less, 2 days or less, or 1 day or less. Cultivation is optionally carried out at temperatures from about 4° C. to about 30° C., e.g., from about 18° C. to about 28° C. Cultivation can include aeration-shaking culture, shaking culture, stationary culture, batch culture, semi-continuous culture, continuous culture, rolling batch culture, wave culture, or the like. Cultivation can be performed using a conventional agitation-fermenter, a bubble column fermenter (batch or continuous cultures), a wave fermenter, etc.

Cultures can be aerated by one or more of a variety of methods, including shaking Optionally, shaking ranges from about 100 rpm to about 1000 rpm, e.g., from about 350 rpm to about 600 rpm or from about 100 to about 450 rpm. Optionally, the cultures are aerated using different shaking speeds during biomass-producing phases and during lipid-producing phases. Alternatively or additionally, shaking speeds can vary depending on the type of culture vessel (e.g., shape or size of flask).

Optionally, the level of dissolved oxygen (DO) is higher during the biomass production phase than it is during the lipid production phase. Thus, DO levels are reduced during the lipid production phase (i.e., the DO levels are less than the amount of dissolved oxygen in biomass production phase). Optionally, the level of dissolved oxygen is reduced below saturation. For example, the level of dissolved oxygen can be reduced to a very low, or even undetectable, level.

The production of desirable lipids can be enhanced by culturing cells according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased).

Pasteurization

Optionally, the resulting biomass is pasteurized to kill the cells and inactivate undesirable substances present in the biomass. For example, the biomass can be pasteurized to inactivate compound degrading substances. The biomass can be present in the fermentation media or isolated from the fermentation media for the pasteurization step. The pasteurization step can be performed by heating the biomass and/or fermentation media to an elevated temperature. For example, the biomass and/or fermentation media can be heated to a temperature from about and including 55° C. to about and including 121° C. (e.g., from about and including 55° C. to about and including 90° C. or from about and including 65° C. to about and including 80° C.). Optionally, the biomass and/or fermentation media can be heated from about and including 4 minutes to about and including 120 minutes (e.g., from about and including 30 minutes to about and including 120 minutes, or from about and including 45 minutes to about and including 90 minutes, or from about and including 55 minutes to about and including 75 minutes). The pasteurization can be performed using a suitable heating means as known to those of skill in the art, such as by direct steam injection.

Optionally, a pasteurization step is not performed (i.e., the method lacks a pasteurization step).

Harvesting and Washing

Optionally, the biomass can be harvested according to methods known to those of skill in the art. For example, the biomass can optionally be collected from the fermentation media using various conventional methods, such as centrifugation (e.g., solid-ejecting centrifuges) or filtration (e.g., cross-flow filtration) and can also include the use of a precipitation agent for the accelerated collection of cellular biomass (e.g., sodium phosphate or calcium chloride).

Optionally, the biomass is washed with water. Optionally, the biomass can be concentrated up to about and including 30% solids. For example, the biomass can be concentrated to about and including 5% to about and including 30% solids, from about and including 7.5% to about and including 15% solids, or from about and including 15% solids to about and including 20% solids, or any percentage within the recited ranges. Optionally, the biomass can be concentrated to about 30% solids or less, about 29% solids or less, about 28% solids or less, about 27% solids or less, about 26% solids or less, about 25% solids or less, about 24% solids or less, about 23% solids or less, about 22% solids or less, about 21% solids or less, about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

Hydrolysis

Cell hydrolysis (i.e., cell disruption) can be performed using chemical, enzymatic, and/or mechanical methods. Optionally, the method described herein lacks a drying step. For example, the biomass is optionally not dried prior to cell hydrolysis. Optionally, the biomass is not concentrated after fermentation is complete and prior to the contacting step.

Chemical methods for hydrolyzing the cells can include adding acid to the cells, which is referred to herein as acid hydrolysis. In the acid hydrolysis method, the biomass can be washed with water using, for example, centrifugation, and concentrated as described above prior to hydrolyzing the cells. Optionally, the biomass is concentrated to about 15% solids with water.

Acid is then added to the washed, wet biomass. Optionally, the biomass is not dried prior to adding the acid. Suitable acids for use in the acid hydrolysis step include sulfuric acid, hydrochloric acid, phosphoric acid, hydrobromic acid, nitric acid, perchloric acid, and other strong acids as known to those of skill in the art. A suitable amount of acid can added to the washed, wet biomass to achieve a final concentration of from about and including 100 mM to about and including 200 mM (e.g., from about and including 120 mM to about and including 180 mM or from about and including 140 mM to about and including 160 mM). Sulfuric acid can be added to the washed, wet biomass to a final concentration of 160 mM.

The resulting mixture including water, biomass, and acid can then be incubated for a period of time to hydrolyze the cells. Optionally, the mixture can be incubated at a temperature of from about and including 30° C. to about and including 200° C. For example, the mixture can be incubated at a temperature of from about and including 45° C. to about and including 180° C., from about and including 60° C. to about and including 150° C., or from about and including 80° C. to about and including 130° C. Optionally, the mixture is incubated in an autoclave at a temperature of 121° C. The mixture can be incubated for a period of time suitable to hydrolyze at least 50% of the cells (e.g., at least 60% of the cells, at least 70% of the cells, at least 80% of the cells, at least 90% of the cells, at least 95% of the cells, or 100% of the cells). The period of time for incubating the cells depends on the incubation temperature. Incubating the mixture at a higher temperature can result in the hydrolysis proceeding at a faster rate (i.e., requiring a shorter period of time for hydrolysis). In some examples, the cells can be incubated at 60° C. for 1 hour.

As described above, cell hydrolysis (i.e., cell disruption) can be performed using enzymatic methods. Specifically, the population of microorganisms can be contacted with one or more enzymes under conditions that cause disruption of the microorganisms. Optionally, the enzyme is a protease. An example of a suitable protease is ALCALASE 2.4L FG (Novozymes; Franklinton, N.C.). Optionally, the cells are not washed with water prior to the enzymatic hydrolysis. Optionally, the population of microorganisms is not concentrated prior to the enzymatic hydrolysis.

Prior to contacting the microorganisms with the one or more enzymes, the pH of the fermentation media can optionally be adjusted to from about and including 5 to 8.5, e.g., from about and including 5.5 to 8.0 or from about and including 6.5 to 7.5, or any value within the recited ranges. For example, the pH of the fermentation media can optionally be adjusted to 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. The pH can be adjusted using, for example, a base such as sodium hydroxide (e.g., 1N NaOH), ammonium hydroxide, calcium hydroxide, magnesium hydroxide, or potassium hydroxide. The pH of the fermentation media can also be adjusted during the contacting step. Optionally, the pH is adjusted to about a pH of 8.0 prior to or during the contacting step.

The microorganisms can be contacted with the one or more enzymes while the population of microorganisms is in the fermentation medium (i.e., the contacting step occurs in the fermentation medium). Optionally, the fermentation medium is concentrated after fermentation and prior to the contacting step. Optionally, the fermentation medium is diluted after fermentation and prior to the contacting step. Optionally, the enzyme added to the fermentation medium is at a concentration of from about 0.001% to about 0.4% volume/volume (v/v). For example, the enzyme added to the fermentation medium can be at a concentration of from 0.05% (v/v) to 0.4% (v/v), 0.05% to 0.2% (v/v), or from 0.1% to 0.2% (v/v). In some examples, the enzyme added to the fermentation medium is at a concentration of 0.05% (v/v), 0.1% (v/v), 0.15% (v/v), 0.2% (v/v), 0.25% (v/v), 0.30% (v/v), 0.35% (v/v), or 0.4% (v/v).

The contacting step can be performed at a temperature of at least about 45° C. Optionally, the contacting step is performed at a temperature of from about and including 45° C. to about and including 70° C., from about and including 50° C. to about and including 70° C., from about and including 55° C. to about and including 70° C., or at 55° C. The contacting step can be performed for a suitable period of time to result in the disruption of the microorganisms. For example, the contacting step can be performed from about and including 1 hour to about and including 20 hours, e.g., from 1 hours to 18 hours, from 1 hour to 6 hours, from 4 hours to 6 hours, or any timeframe within the recited ranges. Optionally, the contacting step can be performed for about 4 hours.

Optimum temperature, time, pH, and enzyme concentration depend on the specific enzyme, and a person of ordinary skill in the art would be able to modify the temperature, time, pH, and enzyme concentration as appropriate for a given enzyme.

Optionally, the contacting step is performed in the presence of either about 0.05% (v/v) or about 0.2% (v/v) enzyme for about 1 to 6 hours at about 55° C. For example, the contacting step can be performed in the presence of 0.1%

(v/v) enzyme for four hours at 55° C. Optionally, the contacting step is performed in the absence of surfactants (i.e., no surfactant is present).

Optionally, the cell disruption can be performed using other chemical and mechanical methods as known to those of skill in the art. For example, cell disruption can be performed using alkaline hydrolysis, bead milling, sonication, detergent hydrolysis, solvent extraction, rapid decompression (i.e., the cell bomb method), or high-shear mechanical methods, contact with a chemical, homogenization, ultrasound, milling, shear forces, French press, cold-pressing, heating, drying, osmotic shock, pressure oscillation, expression of an autolysis gene, or combinations of these.

The method can further comprise a pre-treatment step, wherein the pre-treatment step includes disrupting the cells prior to the contacting step. The pre-treatment step can be performed using a chemical, mechanical, or enzymatic cell disruption method. In other words, cell disruption can be performed using a combination of two or more of the chemical, enzymatic, and/or mechanical methods described herein (e.g., enzymatic hydrolysis in combination with bead-milling). The cell disruption methods can be performed sequentially (e.g., bead-milling followed by enzymatic hydrolysis). Optionally, a chemical or mechanical method can be performed as a first hydrolysis step followed by an enzymatic cell disruption as a second hydrolysis step. In these examples, a lower amount of enzyme can be used in the enzymatic cell disruption step as compared to the amount of enzyme used where only one cell disruption method is performed.

Concentrating

The disrupted microorganisms resulting from the enzymatic hydrolysis can be concentrated by separating and removing fermentation media and to provide the desired concentration of the disrupted microorganisms for subsequent steps. Optionally, the disrupted microorganisms are concentrated by centrifugation and removal of one or more substances to provide the desired concentration. When centrifugation is used, optionally, the centrifugation can provide two or more layers including a heavy layer and a light layer. The heavy layer includes soluble fermentation media components and water and the light layer includes the disrupted microorganisms in the form of lipids and spent biomass. The light layer may further include some water. The light layer may include at least a portion of the lipids and biomass and water in the form of an emulsion.

The concentrating step includes removing one or more substances present in the contacting step. For example, the concentrating step can include aqueous removal. Optionally, the concentrating step includes from about and including 25% to about and including 95% aqueous removal (e.g., about 85% aqueous removal), by volume. Optionally, the concentrating step includes removing at least a portion of the heavy layer, for example, by draining the heavy layer through a valve or by suctioning or decanting off of the heavy layer.

Optionally, the concentrated disrupted microorganisms can be allowed to stand for a period of time prior to recovering oil from the disrupted microorganisms according to the extracting step described below. The concentrated disrupted microorganisms can be allowed to stand for up to 24 hours (e.g., 1 hour, 2 hour, 5 hours, 10 hours, 15 hours, 20 hours, or 24 hours).

Extraction

As described above, lipids are extracted from the disrupted microorganisms at a high temperature in the presence of a salt and in the absence of organic solvents.

The extracting step can be performed at a high temperature. As used herein, high temperature refers to a temperature of at least about 55° C. (e.g., a temperature of from about and including 55° C. to about and including 95° C.). For example, the lipid and biomass mixture can be contacted with a salt, an oil, or a biofuel at a temperature of about 65° C. or above, about 70° C. or above, about 75° C. or above, about 80° C. or above, about 85° C. or above, about 90° C. or above, or about 95° C. or above.

The extracting step is performed in the presence of a salt. The salt can be, for example, sodium sulfate. The concentration of the salt added during the extraction step can be from about and including 1% to about and including 5% (v/v) based on the volume of the extraction mixture (e.g., from about and including 3% to about and including 5% (v/v)). For example, the concentration of salt added during the extraction step can be about 1%, about 2%, about 3%, about 4%, or about 5%.

Lipids are extracted from the disrupted microorganisms in the absence of organic solvent (e.g., $C_5$-$C_{12}$ alkane, chlorinated $C_1$-$C_6$ alkane, $C_1$-$C_6$ alcohol, or supercritical carbon dioxide). As used herein, in the absence of organic solvent means less than about 0.5% solvent based on the weight of the disrupted microorganisms (e.g., less than about 0.4%, less than about 0.3%, less than about 0.2%, less than about 0.1%, less than about 0.05%, less than about 0.01%, less than about 0.005%, or 0%).

Optionally, the lipids can be extracted from the disrupted microorganisms by adding an oil (e.g., coconut oil) or biofuel Optionally, the oil added during the extraction step can be a nutritional oil (e.g., an oil derived or obtained from a nutritional source). Examples of suitable nutritional oils for use in the methods described herein include coconut oil, palm oil, canola oil, sunflower oil, soy oil, corn oil, olive oil, safflower oil, palm kernel oil, cottonseed oil, and combinations thereof. Derivatives of any of those oils, such as alkylated derivatives (e.g., methylated or ethylated oils), also could be used.

As used herein, biofuel refers to any fuel, fuel additive, aromatic, and/or aliphatic compound derived from a biomass starting material. For example, suitable biofuels for use in the methods described herein can be derived from plant sources or algal sources. Examples of suitable sources for biofuel include algae, corn, switchgrass, sugarcane, sugarbeet, rapeseed, soybeans, and the like.

Optionally, biofuels can be obtained by harvesting oils from a biological source and converting the oils into biofuel. Methods of converting oils obtained from biological sources (e.g., oils obtained from plant and/or algal sources) are known to those of skill in the art. Optionally, the methods of obtaining biofuels can include cultivating an oil-producing biomass (e.g., algae), extracting the oil (e.g., algal oil), and converting the oil (e.g., algal oil) to form a biofuel. Optionally, the oil can be converted to a biofuel using transesterification. As used herein, transesterification refers to a process of exchanging an alkoxy group of an ester by another alcohol. For example, a transesterification process for use in the methods described herein can include converting algal oil, e.g., triglycerides, to biodiesel, e.g., fatty acid alkyl esters, and glycerol. Transesterification can be accomplished by using traditional chemical processes such as acid or base catalyzed reactions, or by using enzyme-catalyzed reactions.

As used herein, the term organic solvents does not include biofuels, as that term is defined herein, and does not include nutritional oils, such as coconut oil, palm oil, canola oil, sunflower oil, soy oil, corn oil, olive oil, safflower oil, palm kernel oil, cottonseed oil or alkylated (e.g., methylated or ethylated) derivatives thereof.

Optionally the oil or biofuel used to extract lipids from the disrupted microorganisms is not subsequently removed from the extracted lipids. A subsequent fractionation of the extracted oil, wherein the added oil or biofuel stays with only one of the oil fractions, is not considered removal of the oil or biofuel from the extracted lipid. For example, after recovery the oils described herein may be combined with other oils for use as, or incorporated into, one or more of the products described herein. Any one of those other oils or products, such as a biofuel, may be added to the mixture of lipids and biomass during the extraction step as an alternative to, or in addition to, combining with the recovered oil after the conclusion of the recovery process. Adding the other oil during the extraction step can assist demulsification and separation of the lipid from the spent biomass.

In traditional methods that rely on organic solvent extraction to separate lipid from biomass, the organic solvent must be removed from the lipids after recovery, although typically at least trace amounts of solvent are left behind. In the methods described herein, however, optionally more than about 80% of the oil or biofuel added during the extraction step remains in the recovered oil when it is used as, or incorporation into, a final product. That is, optionally less than about 20% of the oil or biofuel added during the extraction step is removed from the recovered oil prior to its use as, or incorporation into, a final product. For example, optionally less than about 15%, less than about 10%, less than about 5%, less than about 2%, or 0% of the oil or biofuel added during the extraction step is removed from the recovered oil prior to its use as, or incorporation into, a final product.

The disrupted microorganisms or biomass can be mixed with the salt, oil, and/or biofuel for a period of time suitable to extract lipids from the disrupted microorganisms or biomass. For example, the salt, oil, and/or biofuel and disrupted microorganisms or biomass can be mixed for about 10 minutes or more, 20 minutes or more, 30 minutes or more, 40 minutes or more, 50 minutes or more, 1 hour or more, or 2 hours or more. Subsequently, the lipid can be separated from the remaining components of the mixture by centrifuging the solution.

Optionally, at least 65% of the lipids theoretically produced by the microorganisms are extracted from the disrupted microorganisms using this method (i.e., the method provides at least about a 65% yield). For example, the yields of lipids extracted from the disrupted microorganisms can be at least about 70%, at least 75%, at least 80%, or at least 85%.

Alternatively, the extraction step can be performed in the absence of oil or biofuel. For example, the lipids can be extracted using mechanical methods. The hydrolyzed biomass and microorganisms can be centrifuged and the lipids can be separated from the remainder of the components. Separating the oil by centrifugation can optionally include a step of adding sodium sulfate to the biomass emulsion. Optionally, the centrifugation can be performed at a high temperature as described herein (e.g., about 55° C. and above, such as at about 80° C.). Optionally, the lipids are contained in the upper layer of the centrifuged material and can be removed by suction or decanting, for example, from the other material.

Optionally, at least about 65% of the lipids produced by the microorganisms are extracted from the disrupted microorganisms using this method (i.e., the method provides at least a 65% yield). For example, the yields of lipids extracted from the disrupted microorganisms can be at least 70%, at least 80%, or at least 90% of the total amount produced.

III. Products

Polyunsaturated fatty acids (PUFAs) (e.g., DHA, EPA) and other lipids produced according to the method described herein can be utilized in any of a variety of applications, for example, exploiting their biological or nutritional properties. Optionally, the compounds can be used in pharmaceuticals, nutritional oils (e.g., nutritional oil supplements), food supplements, animal feed additives, cosmetics, biofuels and the like. Lipids produced according to the methods described herein can also be used as intermediates in the production of other compounds. Optionally, the lipids produced according to the methods described herein can be incorporated into a final product (e.g., a food or feed supplement, an infant formula, a pharmaceutical, a fuel (e.g., biofuel), etc.)

Suitable food or feed supplements into which the lipids described herein may be incorporated include beverages such as milk, water, sports drinks, energy drinks, teas, and juices; confections such as jellies and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFA) can be incorporated into a pharmaceutical. Examples of such pharmaceuticals include various types of tablets, capsules, drinkable agents, etc. Optionally, the pharmaceutical is suitable for topical application. Dosage forms can include, for example, capsules, oils, granula, granula subtilae, pulveres, tabellae, pilulae, trochisci, or the like.

Optionally, one or more of the produced compounds can be used as or incorporated into a biofuel. For example, biofuels may be produced by transesterification of one or more of the produced compounds. A biofuel may be produced by base catalyzed transesterification of a produced oil, acid catalyzed transesterification of the oil, or conversion of the oil to its fatty acids and then to biofuel.

The lipids produced according to the methods described herein can be incorporated into products as described herein by combinations with any of a variety of agents. For instance, such compounds can be combined with one or more binders or fillers. In some embodiments, products can include one or more chelating agents, pigments, salts, surfactants, moisturizers, viscosity modifiers, thickeners, emollients, fragrances, preservatives, etc., and combinations thereof. The examples below are intended to further illustrate certain aspects of the methods and compositions described herein, and are not intended to limit the scope of the claims.

EXAMPLES

Example 1

Pasteurization, Harvesting and Washing, and Chemical Hydrolysis

Pasteurization

T18 biomass was heated with stirring at 60° C. for 1 hour to pasteurize the cells.

Harvesting and Washing

Pasteurized T18 biomass was centrifuged at 4150 rpm for 20 minutes at ambient temperature to separate the final media from the cell paste. The media was removed, and an equivalent mass of water was added to the cell paste to wash the cells. The cell paste-water mixture was shaken for 1 minute, re-centrifuged, and the aqueous phase was removed.

Chemical Hydrolysis

The water-washed T18 cell paste was adjusted to 150 g/L with water. Subsamples (10 mL) were removed and added to 50 mL centrifuge tubes. Each subsample was treated with acid or base to a final concentration according to Table 1. The mixtures were autoclaved at 121° C. for 15 minutes to hydrolyze the cells. After hydrolysis, the samples were hexane-extracted to determine the percentage of oil recovered by mass balance (FIG. 1). Hydrolysis with 160 mM HCl and $H_2SO_4$ resulted in oil recoveries of greater than 85%.

TABLE 1

| Sample Number | Acid/Base Type | Concentration (mM) | Oil Recovery (%) |
|---|---|---|---|
| 1 | HCl | 40 | 1 |
| 2 | HCl | 100 | 47 |
| 3 | HCl | 160 | 100 |
| 4 | $H_3PO_4$ | 40 | 12 |
| 5 | $H_3PO_4$ | 100 | 3 |
| 6 | $H_3PO_4$ | 160 | 5 |
| 7 | $H_2SO_4$ | 40 | 7 |
| 8 | $H_2SO_4$ | 100 | 68 |
| 9 | $H_2SO_4$ | 160 | 94 |
| 10 | NaOH | 40 | 8 |
| 11 | NaOH | 100 | 40 |
| 12 | NaOH | 160 | 52 |
| 13 | KOH | 40 | 8 |
| 14 | KOH | 100 | 20 |
| 15 | KOH | 160 | 54 |

Example 2

Enzymatic Hydrolysis

Figure 2:
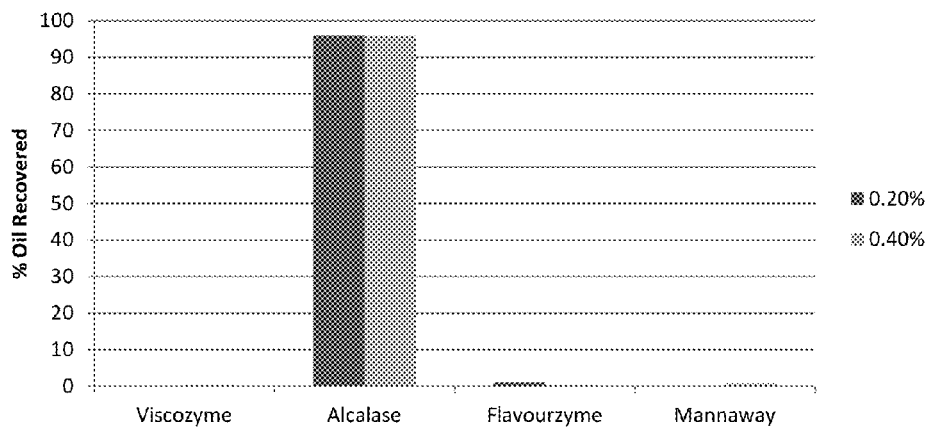
FIG. 2 is a graph showing the percentage of oil recovered from cells enzymatically hydrolyzed with 0.2% (left bar) and 0.4% (right bar) of Viscozyme, Alcalase, Flavourzyme, and Mannaway enzymes.

A water-washed T18 cell paste was adjusted to 220 g/L with water. The pH was adjusted to 7.5 with 1N NaOH. Subsamples (10 mL) were removed and added to 50 mL centrifuge tubes. Each subsample was treated with enzyme according to Table 2. The mixtures were incubated with shaking at 50° C. for 22 hours to hydrolyze the cells. After hydrolysis, the samples were hexane-extracted to determine the percentage of oil recovered by mass balance (FIG. 2). Hydrolysis with Alcalase alone or in combination with another enzyme resulted in oil recoveries of greater than 85%.

TABLE 2

| Sample Number | Enzyme | Concentration (% v/v) | Oil Recovery (%) |
|---|---|---|---|
| 1 | Viscozyme | 0.2 | 0.1 |
| 2 | | 0.4 | 0.3 |
| 3 | Alcalase | 0.2 | 96 |
| 4 | | 0.4 | 96 |
| 5 | Flavourzyme | 0.2 | 1 |
| 6 | | 0.4 | 0.3 |
| 7 | Mannaway | 0.2 | 0 |
| 8 | | 0.4 | 0.8 |
| 9 | Alcalase/Viscozyme | 0.2/0.2 | 93 |
| 10 | Alcalase/Mannaway | 0.2/0.2 | 91 |
| 11 | Flavourzyme/Mannaway | 0.2/0.2 | 0.3 |

Example 3

Acid and Enzymatic Hydrolysis, Effect of Washing

Figure 3:
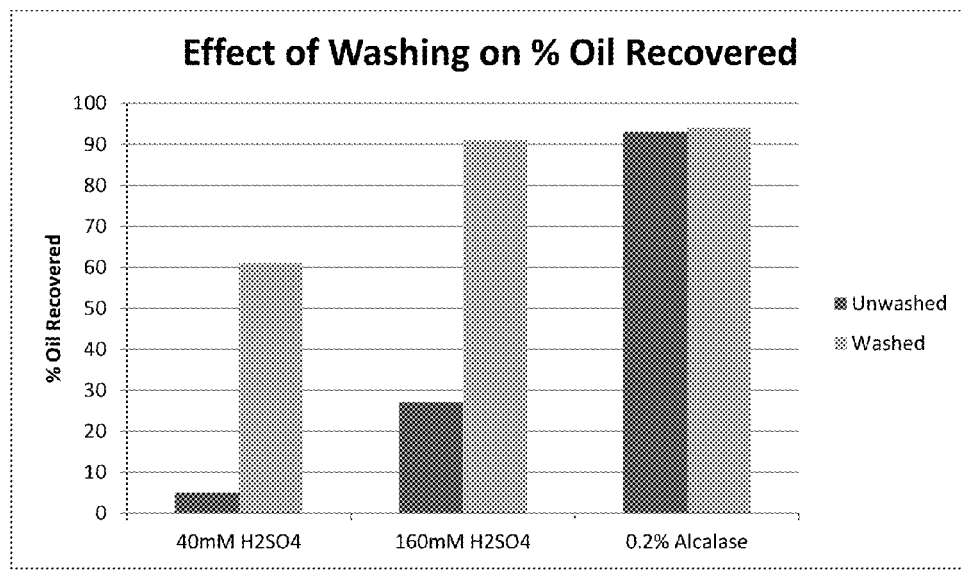
FIG. 3 is a graph showing the percentage of oil recovered from cells not washed (left bar) and washed (right bar) after hydrolysis with 40 mM $H_2SO_4$, 160 mM $H_2SO_4$, and 0.2% (v/v) Alcalase.

Subsamples of pasteurized, nonwashed T18 biomass (10 mL) were added to 50 mL centrifuge tubes. The controls were water-washed, adjusted to 170 g/L water, and subsampled into 50 mL centrifuge tubes. Each subsample was treated with acid or enzyme according to Table 3. The acid hydrolyzed samples were autoclaved at 121° C. for 15 minutes to hydrolyze the cells. The enzymatically hydrolyzed samples were adjusted to pH 7.5 with 1N NaOH and incubated with shaking at 50° C. for 26 hours to hydrolyze the cells. After acid or enzymatic hydrolysis, the samples were hexane-extracted to determine the percentage of oil recovered by mass balance (FIG. 3). Non-washed oil recoveries equivalent to washed oil recoveries were achieved with 0.2% Alcalase hydrolysis.

TABLE 3

| Sample Number | Washed/Not Washed | Acid/Enzyme Treatment | Concentration | Oil Recovered (%) |
|---|---|---|---|---|
| 1 | Not Washed | $H_2SO_4$ | 40 mM | 5 |
| 2 | Washed | $H_2SO_4$ | 40 mM | 61 |
| 3 | Not Washed | $H_2SO_4$ | 160 mM | 27 |
| 4 | Washed | $H_2SO_4$ | 160 mM | 91 |
| 5 | Not Washed | Alcalase | 0.2% v/v | 93 |
| 6 | Washed | Alcalase | 0.2% v/v | 94 |

Example 4

Enzymatic Hydrolysis, Effect of Temperature/Time

Figure 4:
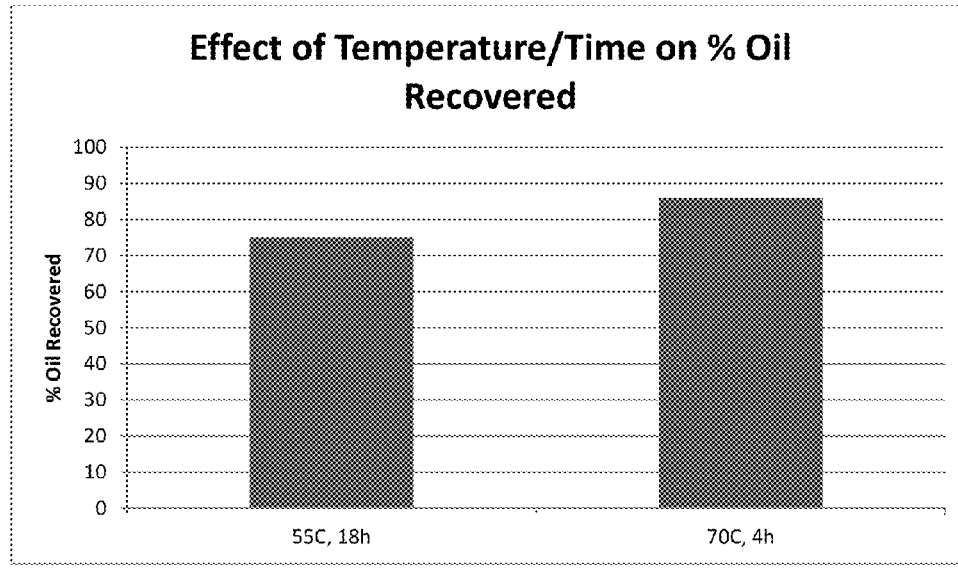
FIG. 4 is a graph showing the percentage of oil recovered from cells enzymatically hydrolyzed at 55° C. for 18 hours and at 70° C. for 4 hours.

The water-washed T18 cell paste was adjusted to 210 g/L with water. The pH was adjusted to 7.5 with 1N NaOH. Subsamples (10 mL) were added into 50 mL centrifuge tubes. Each subsample was treated with 0.2% v/v Alcalase. The mixtures were incubated with shaking at 70° C. for 4 hours to hydrolyze the cells. The controls were incubated with shaking at 55° C. for 18 hours. After hydrolysis, the samples were hexane-extracted to determine the percentage of oil recovered by mass balance (FIG. 4). By increasing the temperature to 70° C., oil recoveries equivalent to hydrolyzing at 55° C. for 18 hours were achieved in 4 hours.

Example 5

Enzymatic Hydrolysis, Extraction with Biofuel

Figure 5:
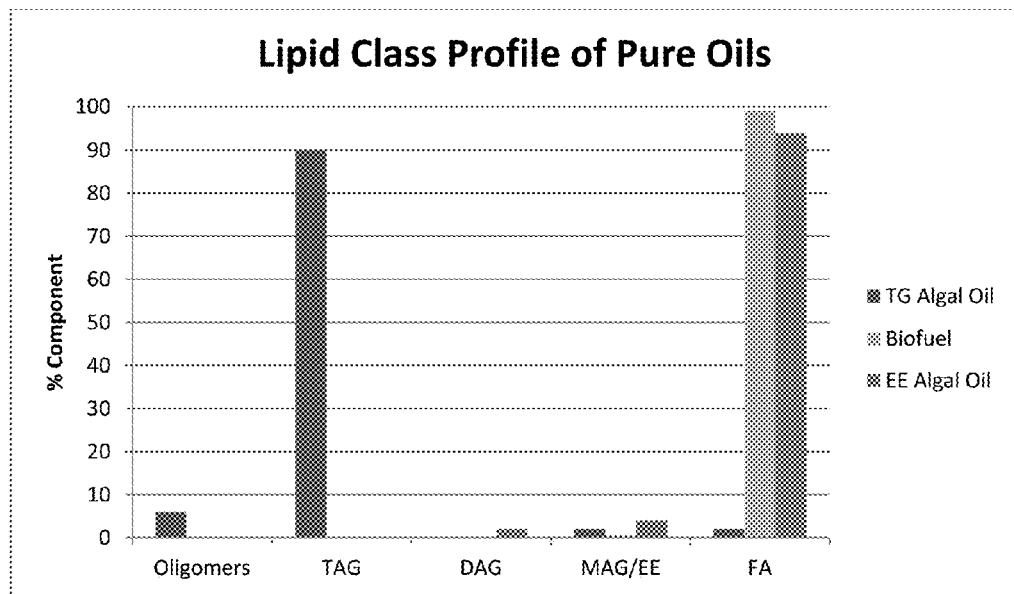
FIG. 5 is a graph showing the lipid class profile of TG algal oil, biofuel and EE algal oil.

The water-washed T18 cell paste was adjusted to 200 g/L with water, and the pH was adjusted to 7.5 with 1N NaOH. Subsamples (10 mL) were removed and added to 50 mL centrifuge tubes. Each subsample was treated with 0.2% v/v Alcalase. The mixtures were incubated with shaking at 55° C. for 18 hours to hydrolyze the cells. After hydrolysis, each subsample was extracted with biofuel according to Table 5 and the percentage of oil was determined by mass balance and based on the lipid class profile of the pure oils (FIG. 5 and Table 5). Extraction with 1:0.4 (wet biomass:biofuel) resulted in oil recoveries of greater than 85% based on the lipid class profile. Triglyceride (TG) algal oil was ethylated (EE) and used for oil extraction as well as the parent TG oil (Table 6). All ratios of wet biomass:EE algal oil resulted in oil recoveries of greater than 85% based on the lipid class profile.

TABLE 5

| Wet Biomass:Biofuel Ratio | TG:EE-FFA Ratio | % Algal Oil | Actual % Algal Oil | Oil Recovered (%) |
| --- | --- | --- | --- | --- |
| Pure Algal Oil | 52.8 | 100 | | |
| 1:2 | 0.0455 | 4.45 | 7.96 | 56 |
| 1:1 | 0.0764 | 7.44 | 14.7 | 51 |
| 1:0.4 | 0.268 | 20.48 | 23.5 | 96 |
| 1:0.2 | 0.42 | 31.42 | 46.4 | 68 |
| Biofuel | 0.00291 | 0 | | |

TABLE 6

| Wet Biomass:Extraction Oil Ratio | Oil Extraction Efficiency (based on mass balance) (%) | Oil Extraction Efficiency (based on DHA:Oleic Acid ratio) (%) |
| --- | --- | --- |
| Biofuel | | |
| 1:2 | 76 | 56 |
| 1:1 | 54 | 51 |
| 1:0.4 | 59 | 96 |
| 1:0.2 | 54 | 68 |
| TG Algal Oil | | |
| 1:2 | 52 | |
| 1:1 | 40 | |
| 1:0.4 | 34 | |
| 1:0.2 | 43 | |
| EE Algal Oil | | |
| 1:2 | 76 | 100 |
| 1:1 | 70 | 100 |
| 1:0.4 | 75 | 100 |
| 1:0.2 | 83 | 100 |

Example 6

Enzymatic Hydrolysis, Solventless Oil Extraction

A 200 mL non-washed T18 biomass at a 224 g/L solids concentration (159 g/L biomass concentration) was heated to 55° C. and adjusted to pH 8 with 1N NaOH. The sample was treated with 0.4% (v/v) Alcalase and incubated with shaking at 55° C. for 18 hours to hydrolyze the cells. After hydrolysis the sample was centrifuged at 4600 rpm for 20 min at 40° C. to separate the media from the concentrated hydrolyzed biomass. 85% of the media was removed. After aqueous removal, the remaining sample was centrifuged at 4600 rpm for 20 min at 40° C. to separate the oil from the spent biomass. The oil was recovered and the % oil recovered was determined by mass balance. By reducing the aqueous concentration after hydrolysis, an oil recovery of greater than 90% was achieved by solventless oil extraction.

Example 7

Solventless Oil Extraction, Large Scale

Figure 6:
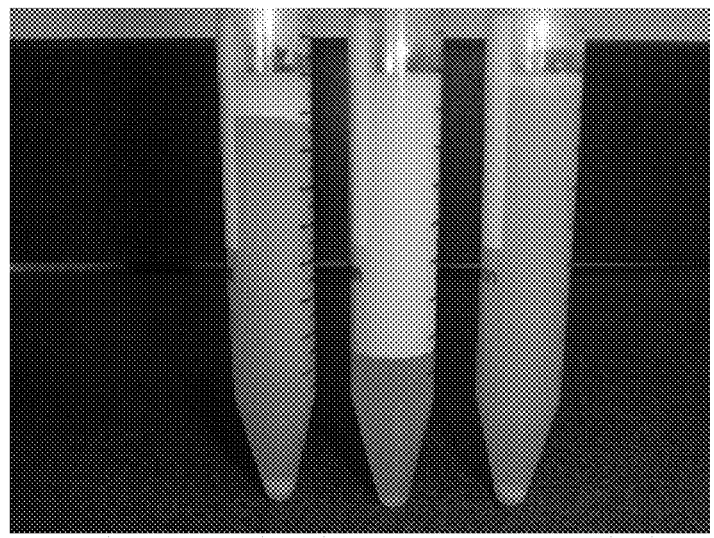
FIG. 6 is a depiction of (left to right) biomass feed hydrolyzed with 0.4% (v/v) Alcalase at 55° C. for 18 hours, concentrated hydrolyzed biomass after centrifugation at 55° C., and media after centrifugation at 55° C.

A 151,400 kg non-washed T18 biomass at a 111 g/L biomass concentration was heated to 55° C. and adjusted to pH 8 with 50N NaOH. 606 L Alcalase was added, the pH was adjusted back to 8, and the mixture was recirculated between 2 vessels to mix for hydrolysis at 55° C. for 18 hours. After hydrolysis, the weight of broth was 160,400 kg. The hydrolyzed biomass was held at 55° C. for centrifugation to separate the media from the concentrated hydrolyzed biomass (FIG. 6). 134,400 kg media was removed and 26,000 kg concentrated hydrolyzed biomass was recovered. The concentrated hydrolyzed biomass was treated with 1300 kg $Na_2SO_4$ and heated with mixing at 90° C. prior to centrifugation to separate the oil from the spent biomass (FIG. 7). 7606 kg oil was recovered for a total oil recovery of 82%. The peroxide value (PV) and acid value (AV) of the recovered oil were 0.4 meq/kg and 0.38 mg KOH/g respectively.

Example 8

Optimized Enzyme Concentration/Time (0.1% Enzyme)

A non-washed T18 biomass sample at a 143 g/L biomass concentration was heated to 55° C. and adjusted to pH 8.0 with 1N NaOH. 25 mL subsamples were removed into 50 mL centrifuge tubes. Each subsample was treated according to Table 7. The mixtures were incubated with shaking at 55° C. to hydrolyze the cells. After hydrolysis the samples were placed in a 100° C. bath for 20 min to deactivate the enzyme. After enzyme deactivation, the samples were centrifuged at 4600 rpm for 20 min at 40° C. to separate the media from the concentrated hydrolyzed biomass. Approximately 80% of the media was removed. The media was passed through a 0.25 um filter and the degree of hydrolysis was determined by the o-pthaldialdehyde (OPA) method (Spellman, D., McEvoy, E., O'Cuinn, G., and Fitz, G. R. J. 2003. Proteinase and exopeptidase hydrolysis of whey protein: Comparison of the TNBS, OPA and pH stat methods for quantification of degree of hydrolysis. *International Dairy Journal*, 13: 447-453). See Table 7.

The concentrated hydrolyzed biomass was treated with 5% (w/v) $Na_2SO_4$ and heated with shaking at 70° C. for 60 min. After treatment, the samples were centrifuged at 4600 rpm for 20 min at 40° C. to separate the oil from the spent biomass. The oil was recovered and the % oil recovered was determined by mass balance (FIG. 8). Hydrolysis with 0.1% Alcalase was complete after 4 hours.

TABLE 7

| Sample Number | Enzyme Concentration (% v/v) | Hydrolysis Time (h) | Oil recovery (%) | Amino Acid Concentration (mM) |
| --- | --- | --- | --- | --- |
| 1 | 0 | 0 | <5% | 26.4 |
| 2 | 0.1 | 0 | 82.6 | 38.2 |
| 3 | 0 | 2 | <5% | 24.3 |

TABLE 7-continued

| Sample Number | Enzyme Concentration (% v/v) | Hydrolysis Time (h) | Oil recovery (%) | Amino Acid Concentration (mM) |
|---|---|---|---|---|
| 4 | 0.1 | 2 | 83.9 | 41.5 |
| 5 | 0 | 4 | <5% | 22.6 |
| 6 | 0.1 | 4 | 86.1 | 46.3 |
| 7 | 0 | 6 | <5% | 23.6 |
| 8 | 0.1 | 6 | 85.9 | 47.5 |
| 9 | 0 | 24 | <5% | 23.5 |
| 10 | 0.1 | 24 | 89.1 | 51.5 |

Example 9

Optimized Enzyme Concentration/Time (0.05% Enzyme)

A non-washed T18 biomass sample at a 143 g/L biomass concentration was heated to 55° C. and adjusted to pH 8.0 with 1N NaOH. 25 mL subsamples were removed into 50 mL centrifuge tubes. Each subsample was treated according to Table 8. The mixtures were incubated with shaking at 55° C. to hydrolyze the cells. After hydrolysis the samples were placed in a 100° C. bath for 20 min to deactivate the enzyme. After enzyme deactivation the samples were centrifuged at 4600 rpm for 20 min at 40° C. to separate the media from the concentrated hydrolyzed biomass. Approximately 80% of the media was removed. The media was passed through a 0.25 um filter and the degree of hydrolysis was determined by the OPA method (Table B).

Figure 9:
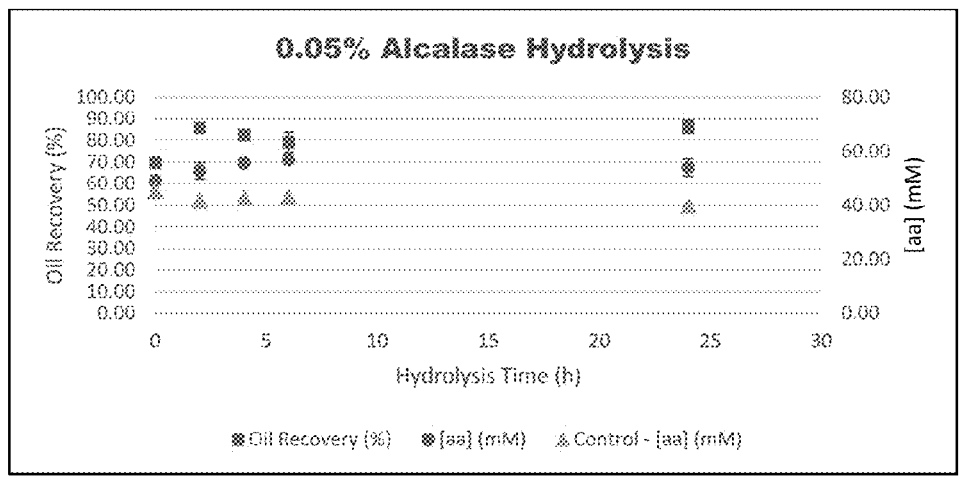
FIG. 9 is a graph showing percentage of oil recovered from cells and the amino acid concentration in the media after enzymatic hydrolysis with 0.05% (v/v) Alcalase at 55° C. and pH 8.0 as a function of hydrolysis time.

The concentrated hydrolyzed biomass was treated with 5% (w/v) $Na_2SO_4$ and heated with shaking at 70° C. for 60 min. After treatment, the samples were centrifuged at 4600 rpm for 20 min at 40° C. to separate the oil from the spent biomass. The oil was recovered and the % oil recovered was determined by mass balance (FIG. 9). Hydrolysis with 0.05% Alcalase was complete after 6 hours.

TABLE 8

| Sample Number | Enzyme Concentration (% v/v) | Hydrolysis Time (h) | Oil recovery (%) | Amino Acid Concentration (mM) |
|---|---|---|---|---|
| 1 | 0 | 0 | <5% | 45.2 |
| 2 | 0.05 | 0 | 69.7 | 49.0 |
| 3 | 0 | 2 | <5% | 41.7 |
| 4 | 0.05 | 2 | 85.7 | 52.6 |
| 5 | 0 | 4 | <5% | 42.8 |
| 6 | 0.05 | 4 | 82.5 | 55.6 |
| 7 | 0 | 6 | <5% | 43.1 |
| 8 | 0.05 | 6 | 79.1 | 56.9 |
| 9 | 0 | 24 | <5% | 39.9 |
| 10 | 0.05 | 24 | 86.2 | 53.9 |

Example 10

Figure 10:
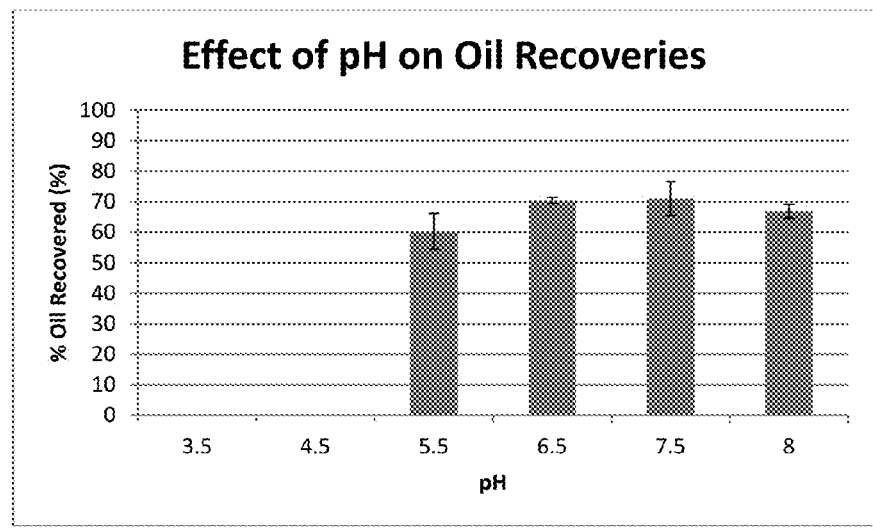
FIG. 10 is a graph showing the percentage of oil recovered from cells enzymatically hydrolyzed at pH 3.5, 4.5, 5.5, 6.5, 7.5, and 8.0.

Enzymatic Hydrolysis, Low pH 150 mL subsamples of non-washed T18 were removed to a 250 mL beaker. Each subsample was treated with 1M HCl or NaOH to adjust to the desired pH according to Table 9. 30 mL subsamples of each pH condition were removed to 50 mL centrifuge tubes. Each subsample was treated with 0.5% (v/v) Alcalase. The mixtures were incubated with shaking at 55° C. for 16 hours to hydrolyze the cells. After hydrolysis the samples were centrifuged at 4600 rpm for 20 min at 40° C. to separate the media from the concentrated hydrolyzed biomass. Approximately 60% media was removed. The concentrated hydrolyzed biomass was treated with 5% (w/v) $Na_2SO_4$ and heated with shaking at 70° C. for 60 min to separate the oil from the spent biomass. The oil was recovered and the % oil recovered solventlessly was determined by mass balance. FIG. 10. Equivalent oil recoveries were achieved at pH 5.5 and 8.

TABLE 9

| Sample Number | pH for Hydrolysis | Oil Recovery (%) |
|---|---|---|
| 1 | 8 | 66.9 ± 2.3 |
| 2 | 3.5 | 0 |
| 3 | 4.5 | 0 |
| 4 | 5.5 | 60.3 ± 5.9 |
| 5 | 6.5 | 70.4 ± 1.0 |
| 6 | 7.5 | 71.0 ± 5.6 |

Example 11

Enzymatic Hydrolysis, Alternate Enzymes 30 mL subsamples of non-washed T18 biomass were removed to 50 mL centrifuge tubes. Each subsample was treated with 0.5% (v/v) enzyme and according to Table 9. The mixtures were incubated with shaking at 55° C. to hydrolyze the cells. After hydrolysis the samples were centrifuged at 4600 rpm for 20 min at 40° C. to separate the media from the concentrated hydrolyzed biomass. Approximately 50% media was removed. The concentrated hydrolyzed biomass was treated with 5% (w/v) $Na_2SO_4$ and heated with shaking at 70° C. for 60 min. After treatment, the samples were hexane extracted to determine the % oil recovered by mass balance. Although no alternate enzyme was identified as being as efficient as Alcalase for hydrolysis, select enzymes (Protease 'M', Savinase Ultra, Blaze Evity, or Polarzyme) could be used in place of Alcalase if necessary.

TABLE 10

| Sample Number | Biomass Concentration (g/L) | Enzyme | pH | Oil Recovery (%) |
|---|---|---|---|---|
| 1 | 171 | Alcalase | 8 | 89 |
| 2 | 171 | Protease 'M' | 6 | 64 |
| 3 | 171 | Cellulase 'A' | 4.5 | 6.7 |
| 4 | 171 | Hemicellulase 90 | 4.5 | 6.1 |
| 5 | 171 | Protease/Cellulose/Hemicellulose | 5 | 28 |
| 6 | 171 | Protease/Cellulose | 5 | 12 |
| 7 | 171 | Protease/Hemicellulose | 5 | 20 |
| 8 | 171 | Cellulose/Hemicellulose | 4.5 | 5.0 |
| 9 | 138 | Alcalase | 8 | 98 |
| 10 | 138 | Savinase Ultra | 8 | 94 |
| 11 | 138 | Blaze Evity | 8 | 93 |
| 12 | 138 | Neutrase | 8 | 7.2 |
| 13 | 150 | Alcalase | 8 | 92 |
| 14 | 150 | Polarzyme | 8 | 88 |

Example 12

Mechanical Hydrolysis

A non-washed T18 biomass sample at a 180 g/L biomass concentration was fed into a 300 mL Dyno-Mill Multi Lab stainless steel chamber loaded with 0.6-0.8 mm zirconium oxide grinding media (80% (v/v) bead volume). In the continuous mode, the bead mill was operated at impeller tip speeds of 10 m/s and feed flow rates of 80 mL/min. A subsample of the partially disrupted biomass slurry was passed back through the disrupting chamber for a second pass. The biomass slurries were centrifuged at 4600 rpm for 20 min at 40° C. to separate the oil from the spent biomass. The oil was recovered and the % oil recovered was determined by mass balance. 1 and 2 passes resulted in oil recoveries of 70%.

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of recovering lipids from a population of lipid-producing microorganisms comprising:
   (a) contacting the population of lipid-producing microorganisms with one or more enzymes under conditions that cause disruption of the microorganisms;
   (b) concentrating the disrupted microorganisms with the lipids by (i) producing a heavy layer and a light layer, wherein the light layer comprises substantially all of the disrupted microorganisms and lipids and (ii) removing at least a portion of the heavy layer; and
   (c) extracting lipids from the concentrated disrupted microorganisms and lipids of step (b) at a high temperature in the presence of a salt in the absence of organic solvents, wherein extraction separates the lipids from the microorganisms and wherein the method lacks a pasteurization step prior to the contacting step.

2. The method of claim 1, wherein the contacting step is performed at a pH of from 5 to 8.5.

3. The method of claim 1, wherein the contacting step is performed at a temperature of from about 50° C. to about 70° C.

4. The method of claim 1, wherein the contacting step is performed for one to twenty hours.

5. The method of claim 1, wherein the contacting step is performed for one to eight hours.

6. The method of claim 1, wherein the enzyme is a protease.

7. The method of claim 6, wherein the enzyme is Alcalase 2.4 L.

8. The method of claim 1, wherein the concentration of enzyme is between 0.001 and 0.4% volume/volume.

9. The method of claim 1, wherein the concentration of enzyme is between 0.05 and 0.2% volume/volume.

10. The method of claim 1, wherein the contacting step is performed in the presence of 0.05% to 0.2% enzyme for one to eight hours at about 55° C.

11. The method of claim 1, wherein the contacting step is performed in the absence of surfactants.

12. The method of claim 1, wherein the concentrating step comprises centrifugation.

13. The method of claim 1, wherein the concentrating step comprises 25% to 95% aqueous removal.

14. The method of claim 1, wherein the high temperature during the extraction step is from 75° C. to 95° C.

15. The method of claim 14, wherein the high temperature during the extraction step is 85° C.

16. The method of claim 1, wherein the concentration of salt added during the extraction step is from 1% to 5%.

17. The method of claim 16, wherein the concentration of salt added during the extraction step is from 3% to 5%.

18. The method of claim 1, wherein the salt added during the extraction step is sodium sulfate.

19. The method of claim 1, wherein the extracting step is performed in the presence of oil.

20. The method of claim 19, wherein the oil is coconut oil.

21. The method of claim 1, wherein the extracting step is performed in the presence of biofuel.

22. The method of claim 1, wherein the population of microorganisms is selected from the group consisting of algae, fungi, bacteria and protists.

23. The method of claim 22, wherein the population of microorganisms is selected from the genus *Thraustochytrium, Schizochytrium* and mixtures thereof.

24. The method of claim 23, wherein the population of microorganisms is a *Thraustochytrium* sp. deposited as ATCC Accession No. PTA-6245.

25. The method of claim 1, wherein the lipids comprise docosahexaenoic acid.

* * * * *